US011529738B2

(12) United States Patent
Ng et al.

(10) Patent No.: US 11,529,738 B2
(45) Date of Patent: Dec. 20, 2022

(54) CONTROL SYSTEM AND A METHOD FOR OPERATING A ROBOT

(71) Applicant: NDR Medical Technology Pte. Ltd., Singapore (SG)

(72) Inventors: Ka Wei Ng, Singapore (SG); Qi Yi Lim, Singapore (SG); Wei Qing Lim, Singapore (SG); Jin Quan Goh, Singapore (SG); Darren Yue Yang Cheong, Singapore (SG)

(73) Assignee: NDR Medical Technology Pte. Ltd., Singapore (SG)

( * ) Notice: Subject to any disclaimer, the term of this patent is extended or adjusted under 35 U.S.C. 154(b) by 348 days.

(21) Appl. No.: 16/919,725

(22) Filed: Jul. 2, 2020

(65) Prior Publication Data

US 2022/0001542 A1 Jan. 6, 2022

(51) Int. Cl.
*B25J 9/00* (2006.01)
*B25J 9/16* (2006.01)
(Continued)

(52) U.S. Cl.
CPC ............ *B25J 9/1692* (2013.01); *A61B 34/30* (2016.02); *B25J 13/089* (2013.01); *B25J 19/023* (2013.01);
(Continued)

(58) Field of Classification Search
CPC ...... B25J 9/1692; B25J 13/089; B25J 19/023; B25J 9/1697; B25J 9/1664; B25J 13/08; B25J 19/021; A61B 34/30; A61B 2034/304; A61B 34/32; A61B 90/37; A61B 34/35; A61B 34/10; A61B 34/20; A61B 34/70; A61B 2034/108; A61B 2034/2065;
(Continued)

(56) References Cited

U.S. PATENT DOCUMENTS 10,169,894 B2 * 1/2019 Balasubramanian ........................ G06F 16/9537

* cited by examiner

*Primary Examiner* — Ian Jen
(74) *Attorney, Agent, or Firm* — Fitch, Even, Tabin & Flannery, LLP

(57) ABSTRACT

Control systems and methods for operating a robot are disclosed. The control system includes a robot comprising a fixed end and a manipulator movable relative to the fixed end. The robot is configured to move an elongated tool attached to an end effector of the manipulator within a robot space for aligning the elongated tool with an occluded target, wherein the robot space comprises a 3-dimensional (3D) space with the fixed end as a center. The control system further includes a processor communicatively coupled with the robot and a 3D imaging device. The 3D imaging device is configured to capture 3D images within an imaging space, wherein the imaging space comprises a 3D space with a fixed reference point on the 3D imaging device as a center. The processor is configured to process a preliminary 3D image of the end effector captured by the 3D imaging device to calibrate the robot by integrating the robot space with the imaging space. The processor is further configured to, based on the calibration of the robot, process a 3D image of a body containing the target captured by the 3D imaging device to obtain location data of the target in the integrated space. The processor is further configured to, based on the location data of the target in the integrated space, automatically control the manipulator to align a longitudinal axis of the elongated tool with the target.

20 Claims, 8 Drawing Sheets

(51) Int. Cl.
  *A61B 34/30* (2016.01)
  *G06T 7/73* (2017.01)
  *B25J 13/08* (2006.01)
  *B25J 19/02* (2006.01)
(52) U.S. Cl.
  CPC ...... *G06T 7/74* (2017.01); *G06T 2207/10028* (2013.01)
(58) Field of Classification Search
  CPC ..... A61B 90/36; A61B 2090/364; G06T 7/74; G06T 2207/10028; G06T 2207/10081; G06T 2207/30096; G06T 7/73; G05B 2219/40609
  See application file for complete search history.

CONTROL SYSTEM AND A METHOD FOR OPERATING A ROBOT

FIELD OF INVENTION

The present invention relates broadly to a control system and a method of operating a robot.

BACKGROUND

Many surgical procedures involve percutaneous insertion of needles into a patient's body. In these procedures, the tip of the needle is placed in a lesion, organ, or vessel inside the body for medical processes such as biopsy and drug delivery processes to be carried out. Some examples of surgical procedures requiring needle insertions include vaccinations, blood/fluid sampling, regional anesthesia, tissue biopsy, catheter insertion, cryogenic ablation, electrolytic ablation, brachytherapy, neurosurgery, deep brain stimulation, and various minimally invasive surgeries (MIS).

There are several ways for inserting a needle into a patient's body in a surgery. For example, the surgeon can perform the procedure manually by placing one end of the needle on a patient's skin, and repeatedly tilting the other end of the needle based on real-time imaging data to establish an alignment between the needle and the target. Surgical procedures performed using this method may be prone to human errors. Also, the patient and surgical crew may be exposed to an excessive amount of radiation which could pose potential health hazards.

Medical instruments such as robotic arms and flexible needles have been introduced to automate the surgical procedure. However, most of these instruments that allow remote control by a clinician merely mimic the manual process. Also, the surgical procedures are usually complicated and require a system including multiple medical instruments. However, the medical instruments are usually designed separately and do not integrate well to work together. Thus, the surgical procedures performed using these instruments may compromise the outcome of the surgery.

Due to the surgical errors, the needle may have to be withdrawn for the entire procedure to be repeated. This may aggravate the condition of a patient as multiple punctures of the patient's body may increase the risks to the patient. For serious cases, the patients may suffer complications such as internal haemorrhage and pneumothorax.

A need therefore exists to provide systems and methods that seek to address at least one of the problems above or to provide a useful alternative.

SUMMARY

According to a first aspect of the present invention, there is provided a control system comprising:
a robot comprising a fixed end and a manipulator movable relative to the fixed end, wherein the robot is configured to move an elongated tool attached to an end effector of the manipulator within a robot space for aligning the elongated tool with an occluded target, wherein the robot space comprises a 3-dimensional (3D) space with the fixed end as a center; and
a processor communicatively coupled with the robot and a 3D imaging device, wherein the 3D imaging device is configured to capture 3D images within an imaging space, wherein the imaging space comprises a 3D space with a fixed reference point on the 3D imaging device as a center, wherein the processor is configured to:
process a preliminary 3D image of the end effector captured by the 3D imaging device to calibrate the robot by integrating the robot space with the imaging space;
based on the calibration of the robot, process a 3D image of a body containing the target captured by the 3D imaging device to obtain location data of the target in the integrated space; and
based on the location data of the target in the integrated space, automatically control the manipulator to align a longitudinal axis of the elongated tool with the target.

The processor may be configured to:
process the preliminary 3D image of the end effector to calculate a resultant vector between the fixed reference point and the fixed end of the robot; and
based on the calculated resultant vector, determine a common origin to integrate the robot space and the imaging space.

The processor may be configured to:
process the preliminary 3D image of the end effector to obtain position data of the end effector in the imaging space;
based on the position data of the end effector, calculate a first directional vector between the fixed reference point and the end effector; and
combine the first directional vector and a second directional vector between the end effector and the fixed end of the robot to calculate the resultant vector between the fixed reference point of the 3D imaging device and the fixed end of the robot.

The processor may be configured to:
process the 3D image of the body to extract position data of the target in the imaging space; and
based on the calibration of the robot, convert the position data of the target in the imaging space into the location data of the target in the integrated space.

The manipulator may be configured to perform a coarse adjustment of the elongated tool involving a displacement of the elongated tool along x, y or z axes, and wherein the end effector may comprise an adjustment mechanism configured to perform a fine adjustment of the elongated tool involving adjustment of an angular orientation of the elongated tool relative to a pivot point.

The adjustment mechanism may comprise:
a base;
a platform configured to be parallel to the base; and a plurality of arms linking the base with the platform, the plurality of arms being configured to move the platform along a plane parallel to the base to adjust the angular orientation of the elongated tool.

The adjustment mechanism may comprise parts made of materials with different radiolucencies, and wherein the processor may be configured to process the preliminary 3D image to obtain position data of radiopaque parts of the adjustment mechanism for calibration of the robot.

The processor may be further configured to:
process the 3D image of the body to identify a selected line in alignment with the target; and
generate an imaginary conical space that tapers along the line with an apex of the conical space disposed at the target and an axis of the conical space aligned with the line, wherein the conical space provides a boundary to the fine adjustment process of the adjustment mechanism.

The processor may be further configured to:

automatically control the manipulator to move the elongated tool into the conical space based on the formula $d \leq r(x)-w$ for coarse adjustment of the robot, wherein d=the closest distance between a centre of working radius of the adjustment mechanism and the axis of the conical space;

r (x)=a radius of the conical space corresponding with measurement of d;

w=the maximum working radius of the adjustment mechanism.

According to a second aspect of the present invention, there is provided a system for striking an occluded target using an elongated tool, the system comprising:

a control system as defined in the first aspect; and an actuator to operate the robot, wherein the processor is further configured to calculate a striking distance between the target and a tip of the elongated tool at alignment; and wherein the actuator is configured to advance the elongated tool toward the target based on the angular orientation of the elongated tool at alignment and the striking distance.

According to a third aspect of the present invention, there is provided a method of operating a robot comprising a fixed end and a manipulator movable relative to the fixed end, the method comprising:

receiving a preliminary 3-dimensional (3D) image of an end effector of the manipulator captured by a 3D imaging device;

processing the preliminary 3D image to calibrate the robot by integrating a robot space operable by the robot with an imaging space operable by the 3D imaging device;

based on the calibration of the robot, processing a 3D image of a body containing an occluded target captured by the 3D imaging device to obtain location data of the target in the integrated space; and based on the location data of the target in the integrated space, automatically controlling the manipulator to align a longitudinal axis of an elongated tool attached to the end effector of the manipulator with the target.

Processing the preliminary 3D image of the end effector may comprise:

calculating a resultant vector between the fixed end of the robot and a fixed reference point on the 3D imaging device, wherein the fixed end of the robot is a center of the robot space and the fixed reference point is a center of the imaging space; and based on the calculated resultant vector, determine a common origin to integrate the robot space and the imaging space.

Calculating the resultant vector may comprise:

obtaining position data of the end effector in the imaging space;

based on the position data of the end effector, calculating a first directional vector between the fixed reference point and the end effector; and combining the first directional vector and a second directional vector between the end effector and the fixed end of the robot to calculate the resultant vector between the fixed reference point of the 3D imaging device and the fixed end of the robot.

Processing the 3D image of a body containing the target may comprise:

extracting position data of the target in the imaging space; and based on the calibration of the robot, converting the position data of the target in the imaging space into the location data of the target in the integrated space.

Aligning the elongated tool with the target may comprise a coarse adjustment of the elongated tool involving a displacement of the elongated tool along x, y or z axes and a fine adjustment of the elongated tool involving adjustment of an angular orientation of the elongated tool relative to a pivot point.

Adjusting the angular orientation of the elongated tool may comprise:

actuating a plurality of arms linking a base and a platform of an adjustment mechanism, thereby moving the platform along a plane parallel to the base.

The adjustment mechanism may comprise parts made of materials with different radiolucencies, and wherein the step of processing the preliminary 3D image comprises obtaining position data of radiopaque parts of the adjustment mechanism for calibration of the robot.

The method may further comprise:

identifying a selected line in alignment with the target on the 3D image of the body; and generating an imaginary conical space that tapers along the line with an apex of the conical space disposed at the target and an axis of the conical space aligned with the line, wherein the conical space provides a boundary to the fine adjustment of the elongated tool.

Automatically controlling the manipulator may comprise:

during the coarse adjustment of the robot, automatically controlling the manipulator to move the elongated tool into the conical space based on the formula $d \leq r-w$, wherein d=the closest distance between a centre of working radius of the adjustment mechanism and the axis of the conical space;

r (x)=a radius of the conical space corresponding with measurement of d;

w=the maximum working radius of the adjustment mechanism.

According to a fourth aspect of the present invention, there is provided a method of striking an occluded target using an elongated tool, the method comprising the steps of:

aligning a longitudinal axis of the elongated tool with the target using the method as defined in the third aspect;

calculating a striking distance between the target and a tip of the elongated tool at alignment; and advancing the elongated tool toward the target based on the calculated striking distance.

BRIEF DESCRIPTION OF THE DRAWINGS

Embodiments of the invention are provided by way of example only, and will be better understood and readily apparent to one of ordinary skill in the art from the following written description and the drawings, in which.

DETAILED DESCRIPTION

Figure 1A:
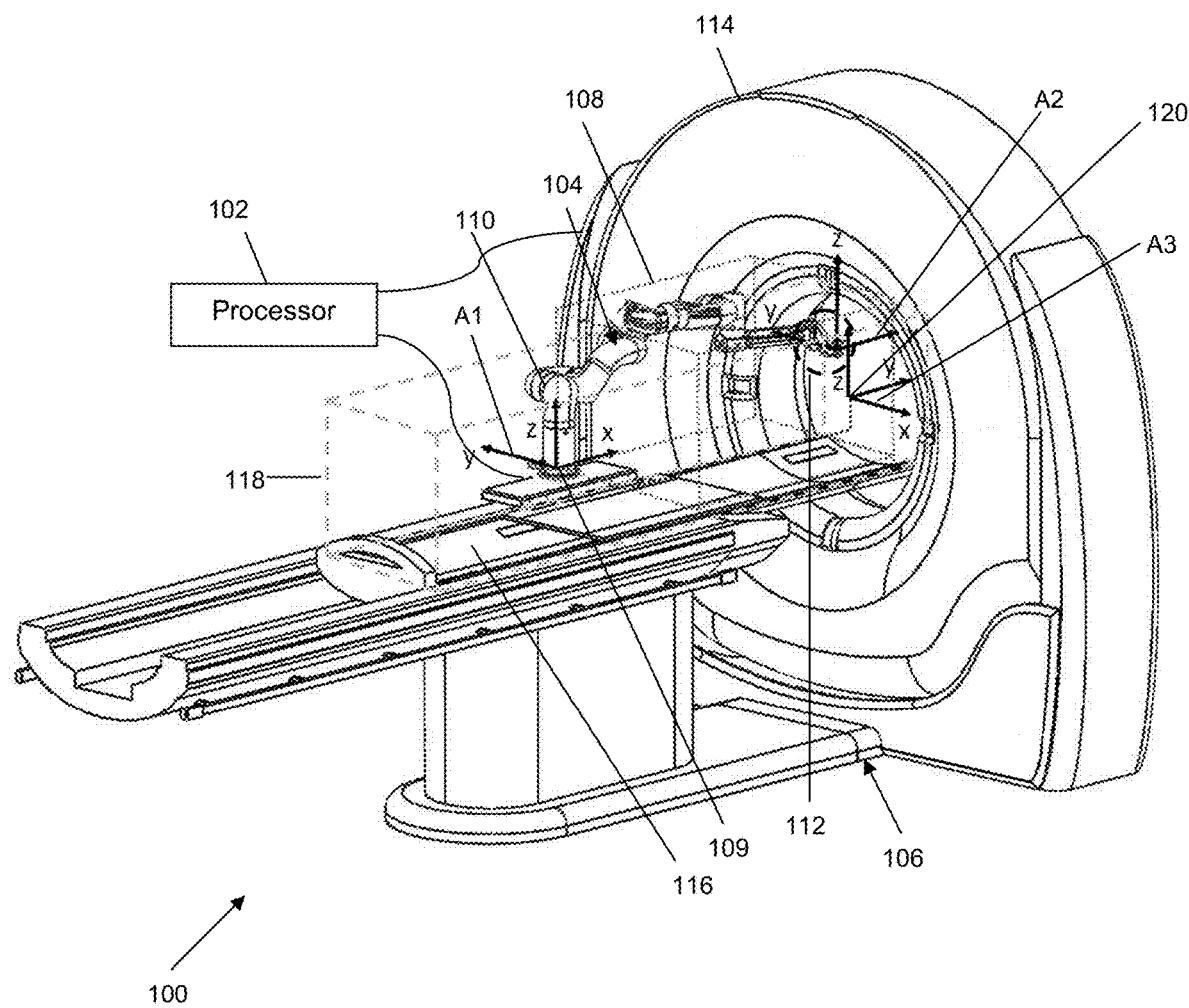
FIG. 1A shows a schematic diagram illustrating a control system according to an example embodiment.
Figure 1B:
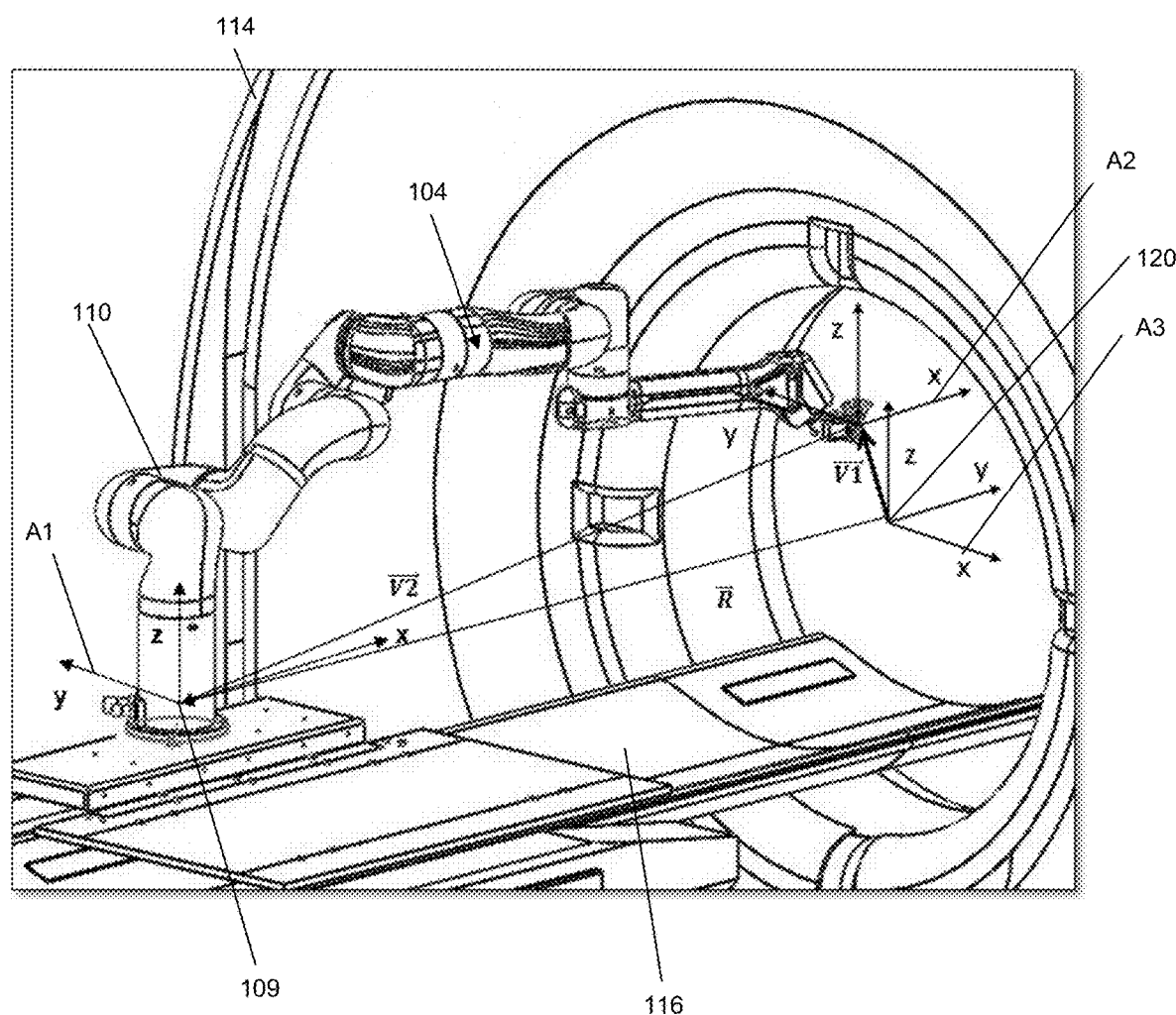
FIG. 1B shows an enlarged view of the system of FIG. 1A.

FIG. 1A shows a schematic diagram illustrating a control system 100 according to an example embodiment. FIG. 1B shows an enlarged view of the system 100 of FIG. 1A. In the description that follows, the system 100 is used to align a surgical tool in a surgical operation performed on a patient's body for treatment of a lesion inside the body. It will be appreciated that the system 100 can also be used in applications other than lesion treatments, such as kidney stone removal and vertebroplasty. Other non-surgical applications are also possible, as will be appreciated by a person skilled in the art.

As shown in FIG. 1A, the system 100 includes a processor 102 that is communicatively coupled to a robot 104 and a 3-dimensional (3D) imaging device 106. As part of the system 100, the robot 104 is configured to move within a 3D space (i.e. hereinafter referred to as "robot space 108") having a fixed center where x, y and z axes meet. The movement of the robot 104 is represented with coordinate axes A1 in FIG. 1A. Based on 3D images captured by the 3D imaging device 106, the robot 104 is controlled by the processor 102 to align the elongated tool to the lesion. The movement of the robot 104 is operated by an actuator (not shown) that receives signals from the processor 102.

In an embodiment, the robot 104 includes a fixed end 109 which is the center of the robot space 108 and a manipulator 110 movable relative to the fixed end 109. The manipulator 110 is used for coarse adjustment of the elongated tool involving a displacement of the elongated tool along x, y or z axes, or combinations thereof. The manipulator includes an adjustment mechanism 112 attached to an end of the manipulator 110 as the end effector of the manipulator 110. The adjustment mechanism 112 is used for fine adjustment of the elongated tool involving adjustment of an angular orientation of the elongated tool relative to a pivot point. The manipulator 110 moves along the coordinate axes A1 while the adjustment mechanism moves along coordinate axes A2 as shown in FIGS. 1A and 1B.

The adjustment mechanism 112 includes a base and a platform configured to be parallel to the base. The base and the platform are linked by a plurality of arms that is configured to move the platform along a plane parallel to the base to adjust the angular orientation of the elongated tool. In an embodiment, the adjustment mechanism includes parts made of materials with different radiolucencies. For example, the platform of the adjustment mechanism 112 includes three balls made of titanium which is a radiopaque material that obstruct x-rays and remaining components of the adjustment mechanism 112 are made of radiolucent materials. The three balls are placed in a uniform angular distance from each other at the annular ring of the platform such that the position of the adjustment mechanism 112 can be accurately determined when it is scanned by the 3D imaging device 106. The configurations of the adjustment mechanism 112 are explained in further detail below with respect to FIGS. 2A to 2C.

The 3D imaging device 106 is a medical imaging device that can perform scanning of the patient's body for producing computer-processed 3D images. Some examples of the 3D imaging device 106 include magnetic resonance imaging (MRI) machine, computerized tomography (CT) scanner and fluoroscope. As shown in FIG. 1A, the 3D imaging device 106 includes a gantry 114 which has an x-ray tube and a bed 116 that can be moved into the gantry 114 while the x-ray tube rotates around the patient on the bed 116. The 3D imaging device 106 is configured to capture 3D image within a 3D space (hereinafter referred to as "imaging space 118"). The imaging space 118 is represented with coordinate axes A3 in FIGS. 1A and 1B with a fixed center (i.e. hereinafter referred to as "a fixed reference point 120") where the x, y and z axes meet.

In use, the 3D imaging device 106 scans the end effector of the robot 104 to produce a preliminary 3D image of the end effector. The processor 102 processes the preliminary 3D image to calibrate the robot 104 by integrating the robot space 108 with the imaging space 118. In an embodiment, the preliminary 3D image of the end effector is processed to obtain position data of the end effector in the imaging space 118. For example, the processor 102 processes the preliminary 3D image to obtain position data of radiopaque parts of the adjustment mechanism 112.

Based on the position data of the end effector, the processor 102 calculates a first directional vector $\overrightarrow{V1}$ between the fixed reference point 120 and the end effector. Further, the processor 102 calculates a second directional vector $\overrightarrow{V2}$ between the end effector and the fixed end 109 of the robot 104. The first directional vector $\overrightarrow{V1}$ and second directional vector V are combined to calculate a resultant vector $\overrightarrow{R}$ between the fixed reference point 120 and the fixed end 109 of the robot 104. Based on the calculated resultant vector $\overrightarrow{R}$, the processor 102 determines a common origin for integration of the robot space 108 and imaging space 118. In an embodiment, the common origin is at the same point as the fixed reference point 120. However, it will be appreciated that the common origin can be located at any other point in a global coordinate system.

Subsequently, the robot 104 is tucked away to the side of the 3D imaging device 106 for the 3D imaging device 104 to scan the patient's body containing the lesion. Based on the calibration of the robot 104, the processor 102 processes the 3D image of the body to obtain location data of the lesion in the integrated space. In an embodiment, the processor 102 processes the 3D image to extract position data of the lesion in the imaging space 118 and based on the calibration of the robot 104, converts the position data in the imaging space 118 into the location data of the lesion in the integrated space. In an embodiment, the processor 102 is further configured to generate a fine adjustment space which provides a boundary to the fine adjustment process of the adjustment mechanism 112.

The processor 102 includes software to process 3D images from the 3D imaging device 106 to obtain location data of body parts, including the body surface, occlusions inside the body (e.g. other organs, bones, arteries) and the lesion. For example, in oncologic imaging, a lesion typically has a richer blood supply than normal body cells which causes an identifiable shade to be generated on 3D images. This allows the software to identify the image of the lesion based on the shades on the 3D images. It will be appreciated that, instead of identifying the lesion using software, the lesion on the 3D image may also be manually identified by a clinician on a display device.

After the location data of the lesion is obtained, the robot 104 is returned to its previous position and above the patient's body. Based on the location data of the lesion, the processor 102 automatically controls the manipulator 110 to align a longitudinal axis of the elongated tool with the lesion. In an embodiment, the 3D imaging device 106 captures real-time 3D images of the body and the end effector of the robot 104, including the surgical tool. During coarse adjustment process, the processor 102 controls the manipulator 110 to move the surgical tool to a position inside the fine adjustment space generated by the processor 102. Next, during fine adjustment process, the processor 102 controls the adjustment mechanism 112 to adjust the angular orientation of the surgical tool within the fine adjustment space to align a longitudinal axis of the surgical tool with the lesion. The coarse and fine adjustment processes are explained in further detail below with respect to FIG. 3.

After aligning the surgical tool, the processor 102 extracts location data of the tip of the surgical tool from the real-time 3D image. Based on the location data of a tip and the lesion, the processor 102 calculates a striking distance between the tip and the lesion. In an embodiment, the processor 102 simulates a trajectory of the surgical tool toward the lesion based on the calculated distance. If the simulation result is satisfactory, the clinician confirms to proceed with the insertion of the surgical tool towards the lesion, either by automatic insertion controlled by the processor 102 or manual insertion controlled by the clinician. Upon receiving confirmation to proceed, the processor 102 sends signals to the actuator to advance the surgical tool toward the lesion based on the calculated striking distance.

Figure 2A:
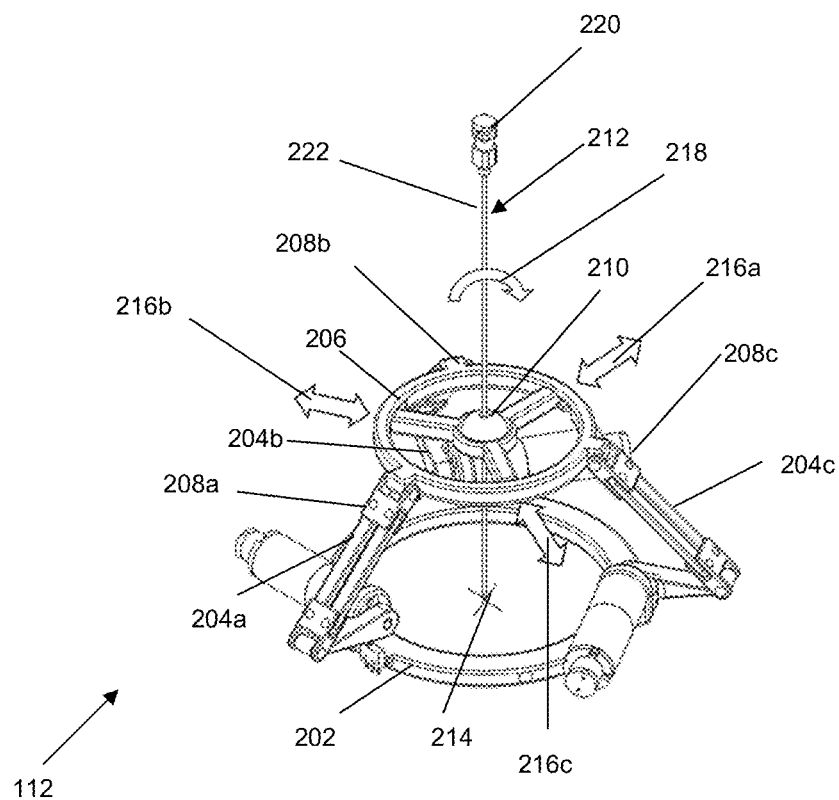
FIG. 2A shows a perspective view of an adjustment mechanism suitable for use in the system of FIGS. 1A and 1B.
Figure 2B:
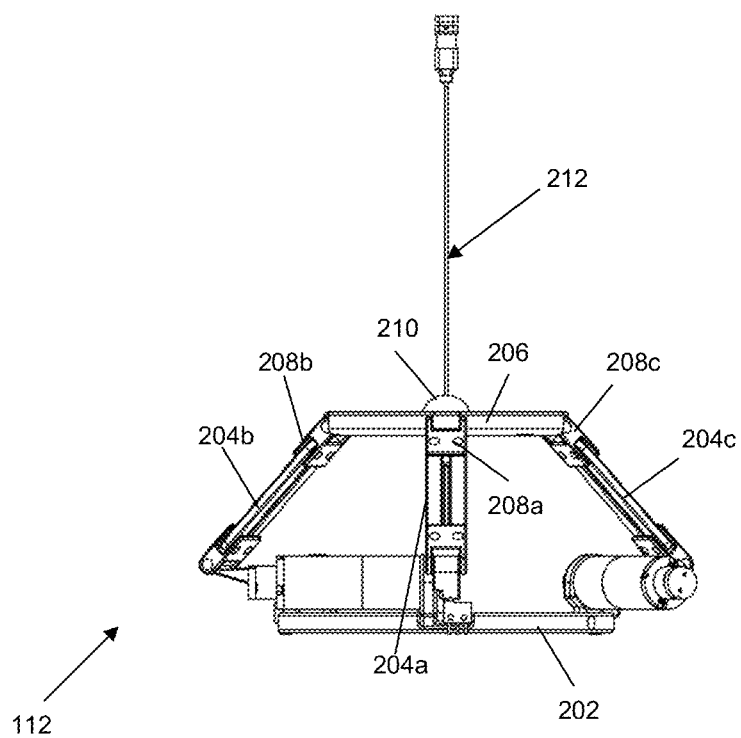
FIG. 2B shows a front view of an adjustment mechanism suitable for use in the system of FIGS. 1A and 1B.

FIGS. 2A and 2B show perspective view and front view respectively of an adjustment mechanism 112 suitable for use in the system 100 of FIGS. 1A and 1B. The adjustment mechanism 112 comprises a base 202, in the form of an annular ring, and a plurality of arms, represented as first arm 204a, second arm 204b and third arm 204c. The arms 204a, 204b, 204c are connected to the base 202 at a substantially uniform angular distance from each other.

The adjustment mechanism 112 further comprises a raised platform 206. The raised platform 206 is connected to end effectors 208a, 208b, 208c of the arms 204a, 204b, 204c respectively. The platform 206 is in the form of an annular ring and comprises a ball joint compliance 210 at the centre of the platform 206. The ball joint compliance 210 comprises a hole which holds a surgical tool 212 and allows sliding movement of the surgical tool 212. The ball joint compliance 210 further comprises a drive mechanism, in the form of a plunger (not shown), for holding and inserting the surgical tool 212 into a patient's body.

During operation, the base 202 is attached to the end of the manipulator 110. The arms 204a, 204b, 204c are actuated by at least one actuator (not shown) to coordinate with each other to adjust the position of the platform 206 and thus the orientation of the surgical tool 212 relative to a pivot point 214. The platform 206 moves relative to the base 202 as shown in FIG. 2A by arrows 216a, 216b, 216c. When the position of the platform 206 is adjusted by the arms 204a, 204b, 204c, the ball joint compliance 210 is held loosely at the center of the platform 206, allowing the surgical tool 212 to pivot or swivel freely about the pivot point 214. This configuration allows tilting of the surgical tool 212 as shown in FIG. 2A by arrow 218.

The surgical tool 212 in the example embodiments comprises an adjustable stopper 220 mounted adjacent to an end 222 of the surgical tool 212 opposite the pivot point 214. After the orientation of the surgical tool 212 and the depth of insertion are confirmed, the position of the ball joint compliance 210 is locked and the stopper 220 is affixed to the surgical tool such that the distance between the stopper 220 and the ball joint compliance 210 is approximately equal to the insertion depth. Next, the plunger is actuated by the actuator to hold and insert the surgical tool 212 into the patient's body. The depth of the insertion of the surgical tool 212 is restricted by the distance between the ball joint compliance 210 and the stopper 220 to avoid an excessive insertion of the surgical tool 212 into the patient's body.

The structure of the adjustment mechanism 112 is typically made of light and rigid material. In an embodiment, different parts of the adjustment mechanism 112 can be made of materials with different radiolucencies. As an example, the platform 206 of the adjustment mechanism 112 includes three balls made of radiopaque material, e.g. stainless steel and titanium, while other parts of the adjustment mechanism 112 are made of radiolucent material. The three balls are placed in a uniform angular distance from each other at the annular ring of the platform such that the position of the adjustment mechanism 112 can be accurately determined when it is scanned by the 3D imaging device 106, allowing a determination of geometrical relationship between the adjustment mechanism 112 and the robot 104 or the 3D imaging device 106.

As the adjustment mechanism 112 has a simple structure and is relatively small in size, it may move and respond fast to signals from the processor 102. The configuration of the adjustment mechanism 112 also restricts excessive movement. This may reduce the tearing of skin in the operation. In addition, most parts of the adjustment mechanism 112 are also made of biocompatible material, such that the use of the adjustment mechanism 112 in the surgery does not cause any undesirable effects to the patient. For example, the materials that may be suitable are titanium and polyether ether ketone (PEEK). However, it will be appreciated that the structure of the adjustment mechanism 112 may be made by other materials.

In an embodiment, the surgical tool 212 may comprise a tactile sensor (not shown) communicatively coupled to the processor 102 to detect pressure change on the surgical tool 212. This may enhance the accuracy of the processor 102 in detecting the depth of the surgical tool 212 in the patient's body and detecting the lesion.

Figure 2C:
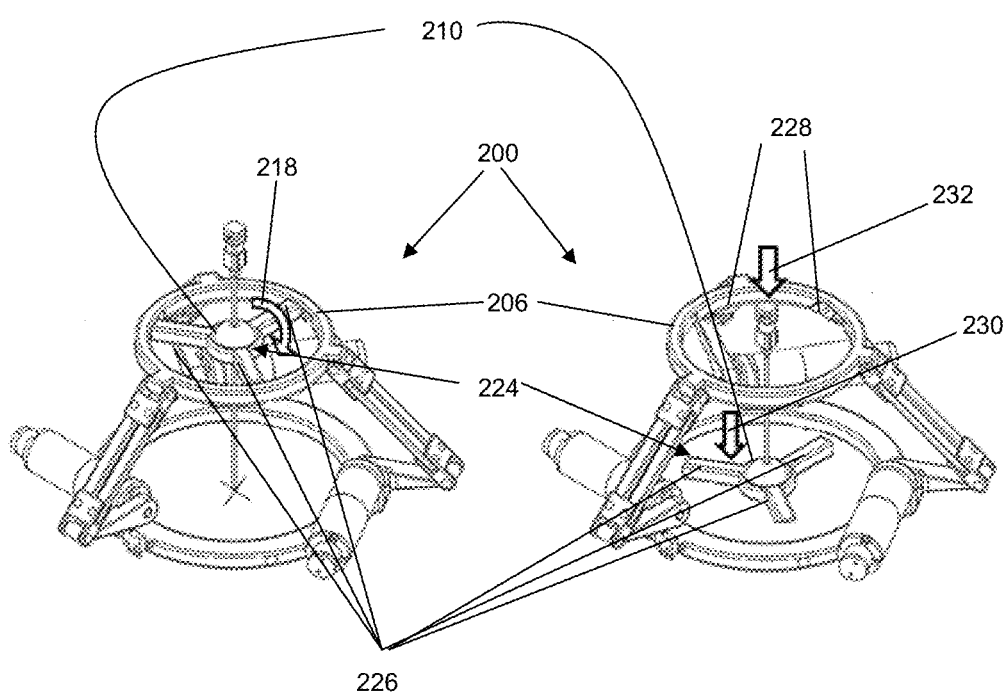
FIG. 2C shows two perspective views illustrating the use of a tool holder of the adjustment mechanism of FIG. 2A.

FIG. 2C shows two perspective views illustrating the use of a tool holder 224 of the adjustment mechanism 112 of FIG. 2A. Here, the tool holder 224 is detachable from the platform 206. The structure of the tool holder 224 includes the ball joint compliance 210 and a plurality of supporting structures 226 extending radially outward from the ball joint compliance 210, linking the ball joint compliance 210 with the annular ring of the platform 206. An engagement mechanism, represented as catch 228, is used for detachably fastening the tool holder 224 to the platform 206.

As shown in the first arrangement (the left diagram on FIG. 2C), the tool holder 224 is attached to the platform 206 when the platform 206 is moved to tilt the surgical tool 212. The tilting of the surgical tool 212 is shown by arrow 218. As shown in the second arrangement (the right diagram on FIG. 2C), if further insertion is required beyond the insertion depth allowed by the stopper 220, the tool holder 224 is detached from the platform 206, e.g. by turning the tool holder 224 in the clockwise or anticlockwise direction, and lowered onto the patient's body, as shown by arrow 230. The tool holder 224 can be mounted on the patient's body, e.g. using adhesive tape or gel. After the tool holder 224 is mounted on the patient's body, the plunger is actuated by the actuator to hold and further insert the surgical tool 212 into the patient's body, as shown by arrow 232. At this point, the angular orientation of the surgical tool has been ascertained to be in alignment with the lesion. The tool holder 224 thus allows the surgical tool 212 to be inserted into the patient's body to a greater depth, providing flexibility in the type of work to be carried out as required.

Figure 3:
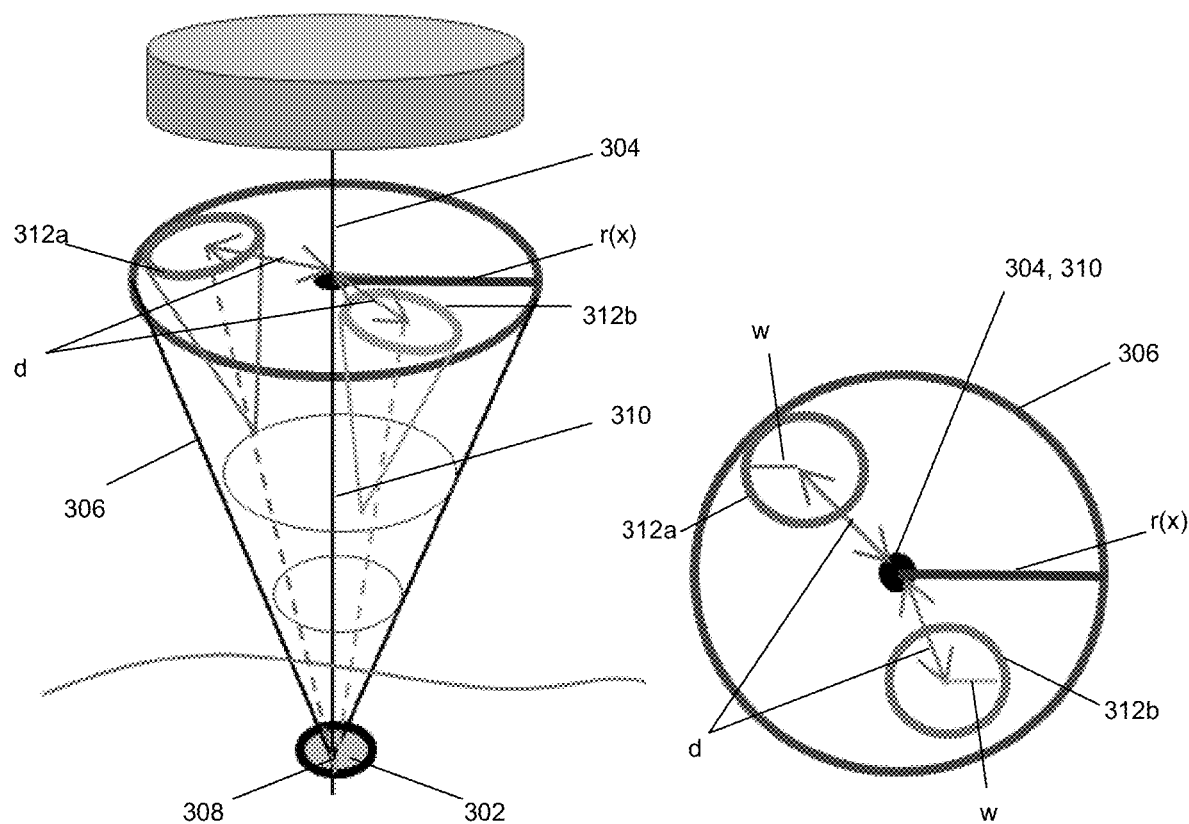
FIG. 3 shows a schematic diagram of a perspective view and a top view of adjustment processes by the system of FIG. 1A and FIG. 1B.

FIG. 3 shows a schematic diagram of a perspective view (on the left) and a top view (on the right) of adjustment processes by the system 100 of FIG. 1A and FIG. 1B.

After the 3D imaging device 106 scans the body, the 3D image of the body containing the lesion 302 is displayed on a display device. Based on the location of the lesion 302 relative to the body surface and occlusions inside the body, the clinician selects a trajectory line 304 which is aligned with the lesion 302 and is suitable for the insertion of the surgical tool to strike the lesion 302. It will be appreciated that, instead of manual selection, the software in the processor 102 can automatically determine one or more trajectory lines for the insertion of the surgical tool to strike the lesion. Specifically, based on the location of the lesion 302, the software can suggest suitable trajectory paths to bypass vital organs so that the surgical tool will not injure the organs and to bypass hard structures such as bones that can bend the surgical tool.

The processor 102 generates an imaginary conical space 306 that tapers along the line 304 with an apex of the conical space 306 disposed at the lesion 302 and an axis 310 of the conical space 306 aligned with the selected line 304. The conical space 306 provides a boundary to the fine adjustment process which involves tilting of the surgical tool relative to a pivot point by the adjustment mechanism 112. In other words, the angular orientation of the surgical tool is adjusted within the conical space 306. This is achieved by the processor 102 during the coarse adjustment of the manipulator 110. Specifically, the processor 102 automatically controls the calibrated robot 104 to move the elongated tool into the conical space 306 based on the formula d≤r (x)−w, wherein d=the closest distance between a centre of working radius of the adjustment mechanism and the axis of the conical space;

r (x)=a radius of the conical space corresponding with measurement of d;

w=the maximum working radius of the adjustment mechanism.

Subsequently, the fine adjustment process is carried out by the adjustment mechanism 112. The surgical tool is tilted within the conical space 306 relative to a pivot point to align the surgical tool with the lesion 302 (as shown on FIG. 3 with two smaller conical spaces 312a, 312b).

Figure 4:
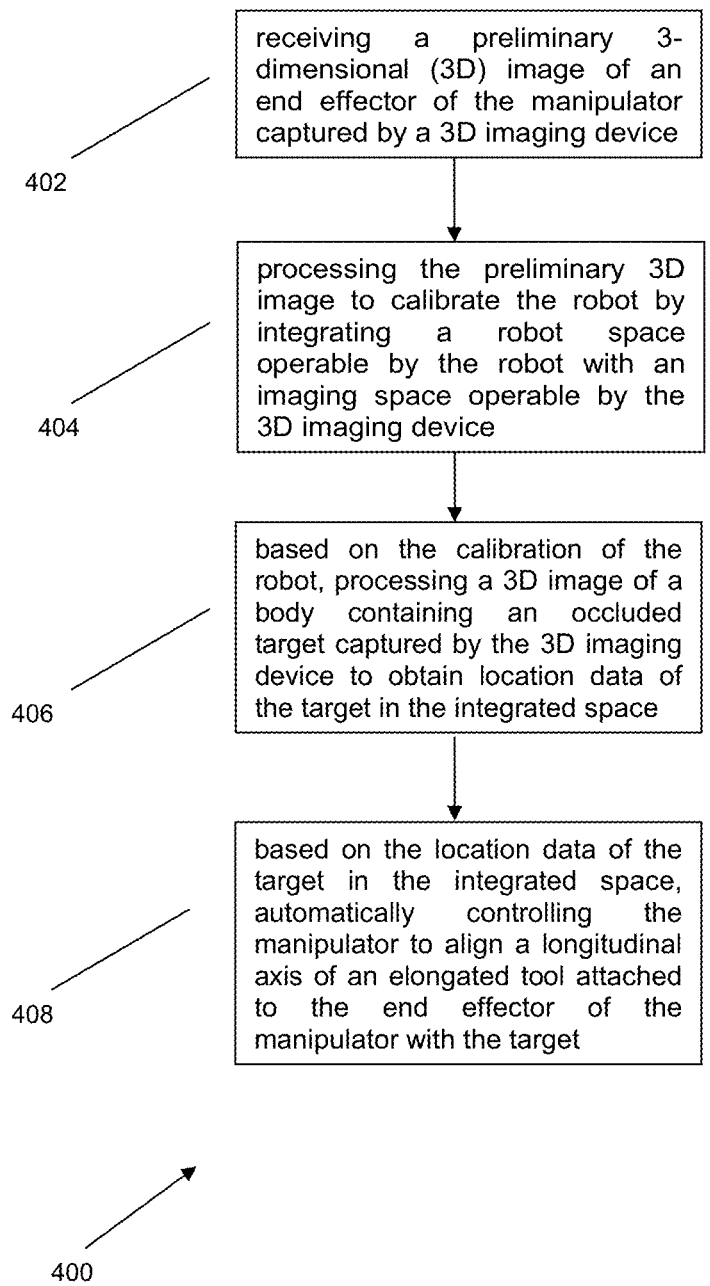
FIG. 4 shows a flow chart illustrating a method of operating a robot.

FIG. 4 shows a flow chart illustrating a method of operating a robot. The robot comprises a fixed end and a manipulator movable relative to the fixed end. At step 402, a preliminary 3-dimensional (3D) image of an end effector of the manipulator captured by a 3D imaging device is received. At step 404, the preliminary 3D image is processed to calibrate the robot by integrating a robot space operable by the robot with an imaging space operable by the 3D imaging device. At step 406, based on the calibration of the robot, a 3D image of a body containing an occluded target captured by the 3D imaging device is processed to obtain location data of the target in the integrated space. At step 408, based on the location data of the target in the integrated space, the manipulator is automatically controlled to align a longitudinal axis of the elongated tool with the target.

Embodiments of the present invention provide a control system and a method of operating a robot. As described above with reference to the figures, the processor 102 calibrates the robot 104 by calculating the resultant vector between the fixed reference point 120 and fixed end 109 to find a common origin. This allows the robot 104 to be calibrated by integrating the robot space 106 and the imaging space 118. The 3D image of the body is then processed to obtained location data of the target in the integrated space and the manipulator 110 is controlled by the processor 102 to align a longitudinal axis of the surgical tool with the target.

The integration of the robot space 108 and imaging space 118 allows on-the spot calibration of the robot 104. Due to the calibration, the robot 104 and the 3D imaging device 106 can work in a synergistic manner and the robot 104 can be controlled by the processor 102 based on 3D images captured by the 3D imaging device to reach a position in the integrated space accurately. This may advantageously enhance the accuracy of the robot 104 in aligning the surgical tool and striking the target, thus reducing the chances of errors in surgical operations. Further, real-time 3D images of the patient's body provide the location data of the target inside the body. This allows the robot 104 to accurately adjust the angular orientation and determine the striking distance between a tip of the surgical tool and the target.

Figure 5:
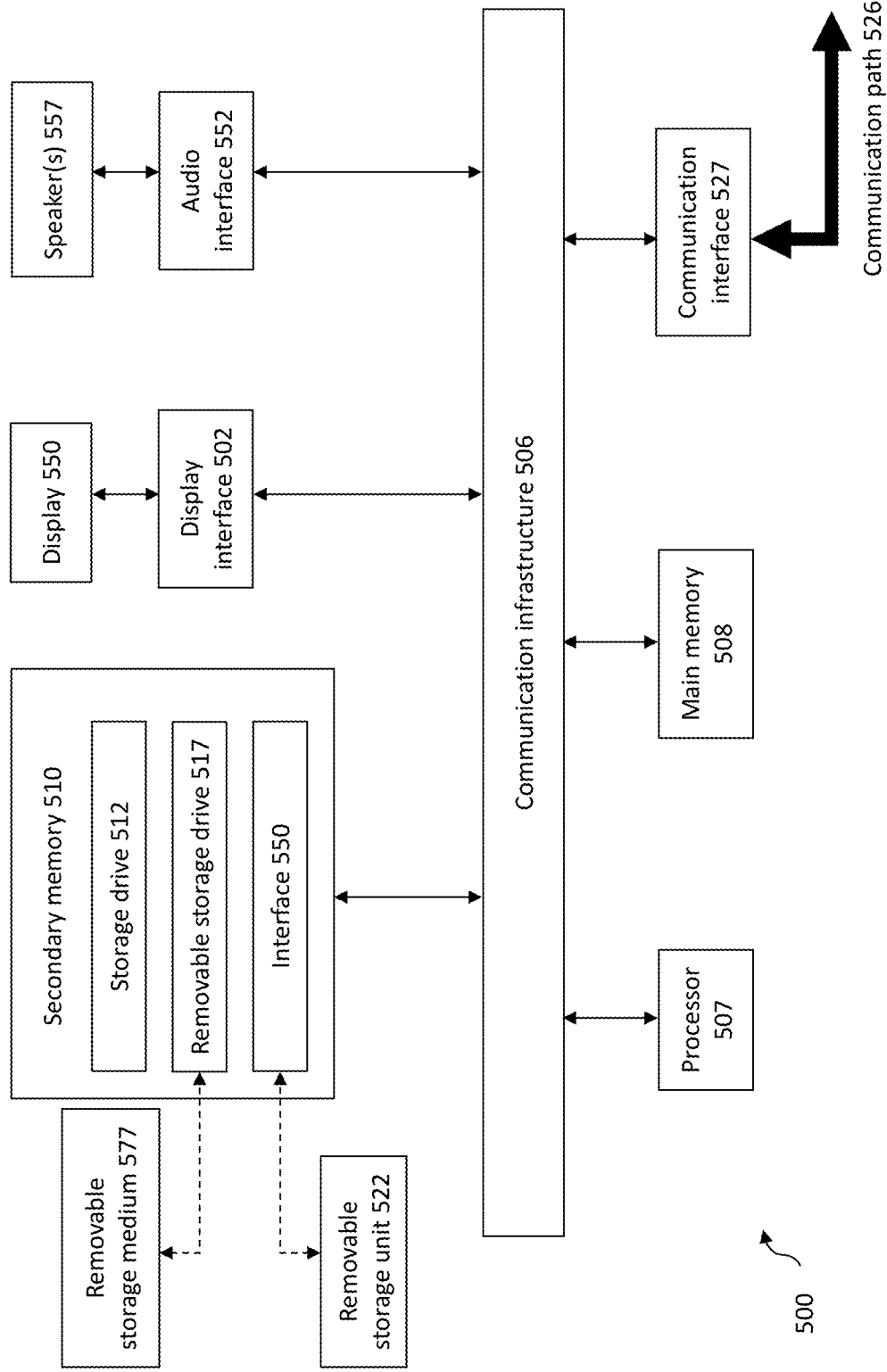
FIG. 5 shows a schematic diagram illustrating a computer suitable for implementing the system and method of the example embodiments.

FIG. 5 depicts an exemplary computing device 500, hereinafter interchangeably referred to as a computer system 500. The exemplary computing device 500 can be used to implement the system 100 shown in FIGS. 1A and 1B and the processes shown in FIGS. 3 and 4. The following description of the computing device 500 is provided by way of example only and is not intended to be limiting.

As shown in FIG. 5, the example computing device 500 includes a processor 507 for executing software routines. Although a single processor is shown for the sake of clarity, the computing device 500 may also include a multi-processor system. The processor 507 is connected to a communication infrastructure 506 for communication with other components of the computing device 500. The communication infrastructure 506 may include, for example, a communications bus, cross-bar, or network.

The computing device 500 further includes a main memory 508, such as a random access memory (RAM), and a secondary memory 510. The secondary memory 510 may include, for example, a storage drive 512, which may be a hard disk drive, a solid state drive or a hybrid drive, and/or a removable storage drive 517, which may include a magnetic tape drive, an optical disk drive, a solid state storage drive (such as a USB flash drive, a flash memory device, a solid state drive or a memory card), or the like. The removable storage drive 517 reads from and/or writes to a removable storage medium 577 in a well-known manner. The removable storage medium 577 may include magnetic tape, optical disk, non-volatile memory storage medium, or the like, which is read by and written to by removable storage drive 517. As will be appreciated by persons skilled in the relevant art(s), the removable storage medium 577 includes a computer readable storage medium having stored therein computer executable program code instructions and/or data.

In an alternative implementation, the secondary memory 510 may additionally or alternatively include other similar means for allowing computer programs or other instructions to be loaded into the computing device 500. Such means can include, for example, a removable storage unit 522 and an interface 550. Examples of a removable storage unit 522 and interface 550 include a program cartridge and cartridge interface (such as that found in video game console devices), a removable memory chip (such as an EPROM or PROM) and associated socket, a removable solid state storage drive (such as a USB flash drive, a flash memory device, a solid state drive or a memory card), and other removable storage units 522 and interfaces 550 which allow software and data to be transferred from the removable storage unit 522 to the computer system 500.

The computing device 500 also includes at least one communication interface 527. The communication interface 527 allows software and data to be transferred between computing device 500 and external devices via a communication path 526. In various embodiments of the inventions, the communication interface 527 permits data to be transferred between the computing device 500 and a data communication network, such as a public data or private data communication network. The communication interface 527 may be used to exchange data between different computing devices 500 which such computing devices 500 form part an interconnected computer network. Examples of a communication interface 527 can include a modem, a network interface (such as an Ethernet card), a communication port (such as a serial, parallel, printer, GPIB, IEEE 1394, RJ45, USB), an antenna with associated circuitry and the like. The communication interface 527 may be wired or may be wireless. Software and data transferred via the communication interface 527 are in the form of signals which can be electronic, electromagnetic, optical or other signals capable of being received by communication interface 527. These signals are provided to the communication interface via the communication path 526.

As shown in FIG. 5, the computing device 500 further includes a display interface 502 which performs operations for rendering images to an associated display 550 and an audio interface 552 for performing operations for playing audio content via associated speaker(s) 557.

As used herein, the term "computer program product" may refer, in part, to removable storage medium 577, removable storage unit 522, a hard disk installed in storage drive 512, or a carrier wave carrying software over communication path 526 (wireless link or cable) to communication interface 527. Computer readable storage media refers to any non-transitory, non-volatile tangible storage medium that provides recorded instructions and/or data to the computing device 500 for execution and/or processing. Examples of such storage media include magnetic tape, CD-ROM, DVD, Blu-Ray™ Disc, a hard disk drive, a ROM or integrated circuit, a solid state storage drive (such as a USB flash drive, a flash memory device, a solid state drive or a memory card), a hybrid drive, a magneto-optical disk, or a computer readable card such as a PCMCIA card and the like, whether or not such devices are internal or external of the computing device 500. Examples of transitory or non-tangible computer readable transmission media that may also participate in the provision of software, application programs, instructions and/or data to the computing device 500 include radio or infra-red transmission channels as well as a network connection to another computer or networked device, and the Internet or Intranets including e-mail transmissions and information recorded on Websites and the like.

The computer programs (also called computer program code) are stored in main memory 508 and/or secondary memory 510. Computer programs can also be received via the communication interface 527. Such computer programs, when executed, enable the computing device 500 to perform one or more features of embodiments discussed herein. In various embodiments, the computer programs, when executed, enable the processor 507 to perform features of the above-described embodiments. Accordingly, such computer programs represent controllers of the computer system 500.

Software may be stored in a computer program product and loaded into the computing device 500 using the removable storage drive 517, the storage drive 512, or the interface 550. The computer program product may be a non-transitory computer readable medium. Alternatively, the computer program product may be downloaded to the computer system 500 over the communications path 526. The software, when executed by the processor 507, causes the computing device 500 to perform functions of embodiments described herein.

It is to be understood that the embodiment of FIG. 5 is presented merely by way of example. Therefore, in some embodiments one or more features of the computing device 500 may be omitted. Also, in some embodiments, one or more features of the computing device 500 may be combined together. Additionally, in some embodiments, one or more features of the computing device 500 may be split into one or more component parts.

When the computing device 500 is configured to calibrate a robot comprising a fixed end and a manipulator movable relative to the fixed end, the computing system 500 will have a non-transitory computer readable medium having stored thereon an application which when executed causes the computing system 500 to perform steps comprising: receiving a preliminary 3-dimensional (3D) image of an end effector of the manipulator captured by a 3D imaging device; processing the preliminary 3D image to calibrate the robot by integrating a robot space operable by the robot with an imaging space operable by the 3D imaging device; based on the calibration of the robot, processing a 3D image of a body containing an occluded target captured by the 3D imaging device to obtain location data of the target in the integrated space; and based on the location data of the target in the integrated space, automatically controlling the manipulator to align a longitudinal axis of an elongated tool attached to the end effector of the manipulator with the target.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A control system comprising:
   a robot comprising a fixed end and a manipulator movable relative to the fixed end, wherein the robot is configured to move an elongated tool attached to an end effector of the manipulator within a robot space for aligning the elongated tool with an occluded target, wherein the robot space comprises a 3-dimensional (3D) space with the fixed end as a center; and
   a processor communicatively coupled with the robot and a 3D imaging device, wherein the 3D imaging device is configured to capture 3D images within an imaging space, wherein the imaging space comprises a 3D space with a fixed reference point on the 3D imaging device as a center, wherein the processor is configured to:
   process a preliminary 3D image of the end effector captured by the 3D imaging device to calibrate the robot by integrating the robot space with the imaging space;

based on the calibration of the robot, process a 3D image of a body containing the target captured by the 3D imaging device to obtain location data of the target in the integrated space; and based on the location data of the target in the integrated space, automatically control the manipulator to align a longitudinal axis of the elongated tool with the target.

2. The system as claimed in claim 1, wherein the processor is configured to:

process the preliminary 3D image of the end effector to calculate a resultant vector between the fixed reference point and the fixed end of the robot; and based on the calculated resultant vector, determine a common origin to integrate the robot space and the imaging space.

3. The system as claimed in claim 2, wherein the processor is configured to:

process the preliminary 3D image of the end effector to obtain position data of the end effector in the imaging space;

based on the position data of the end effector, calculate a first directional vector between the fixed reference point and the end effector; and combine the first directional vector and a second directional vector between the end effector and the fixed end of the robot to calculate the resultant vector between the fixed reference point of the 3D imaging device and the fixed end of the robot.

4. The system as claimed in claim 1, wherein the processor is configured to:

process the 3D image of the body to extract position data of the target in the imaging space; and based on the calibration of the robot, convert the position data of the target in the imaging space into the location data of the target in the integrated space.

5. The system as claimed in claim 1, wherein the manipulator is configured to perform a coarse adjustment of the elongated tool involving a displacement of the elongated tool along x, y or z axes, and wherein the end effector comprises an adjustment mechanism configured to perform a fine adjustment of the elongated tool involving adjustment of an angular orientation of the elongated tool relative to a pivot point.

6. The system as claimed in claim 5, wherein the adjustment mechanism comprises:

a base;

a platform configured to be parallel to the base; and a plurality of arms linking the base with the platform, the plurality of arms being configured to move the platform along a plane parallel to the base to adjust the angular orientation of the elongated tool.

7. The system as claimed in claim 5, wherein the adjustment mechanism comprises parts made of materials with different radiolucencies, and wherein the processor is configured to process the preliminary 3D image to obtain position data of radiopaque parts of the adjustment mechanism for calibration of the robot.

8. The system as claimed in claim 5, wherein the processor is further configured to:

process the 3D image of the body to identify a selected line in alignment with the target; and generate an imaginary conical space that tapers along the line with an apex of the conical space disposed at the target and an axis of the conical space aligned with the line, wherein the conical space provides a boundary to the fine adjustment process of the adjustment mechanism.

9. The system as claimed in claim 8, wherein the processor is configured to:

automatically control the manipulator to move the elongated tool into the conical space based on the formula $d \leq r(x) - w$ for coarse adjustment of the robot, wherein d=the closest distance between a centre of working radius of the adjustment mechanism and the axis of the conical space;

r (x)=a radius of the conical space corresponding with measurement of d;

w=the maximum working radius of the adjustment mechanism.

10. A system for striking an occluded target using an elongated tool, the system comprising:

a control system as claimed in claim 1; and an actuator to operate the robot, wherein the processor is further configured to calculate a striking distance between the target and a tip of the elongated tool at alignment; and wherein the actuator is configured to advance the elongated tool toward the target based on the angular orientation of the elongated tool at alignment and the striking distance.

11. A method of operating a robot comprising a fixed end and a manipulator movable relative to the fixed end, the method comprising:

receiving a preliminary 3-dimensional (3D) image of an end effector of the manipulator captured by a 3D imaging device;

processing the preliminary 3D image to calibrate the robot by integrating a robot space operable by the robot with an imaging space operable by the 3D imaging device;

based on the calibration of the robot, processing a 3D image of a body containing an occluded target captured by the 3D imaging device to obtain location data of the target in the integrated space; and based on the location data of the target in the integrated space, automatically controlling the manipulator to align a longitudinal axis of an elongated tool attached to the end effector of the manipulator with the target.

12. The method as claimed in claim 11, wherein processing the preliminary 3D image of the end effector comprises:

calculating a resultant vector between the fixed end of the robot and a fixed reference point on the 3D imaging device, wherein the fixed end of the robot is a center of the robot space and the fixed reference point is a center of the imaging space; and based on the calculated resultant vector, determine a common origin to integrate the robot space and the imaging space.

13. The method as claimed in claim 12, wherein calculating the resultant vector comprises:

obtaining position data of the end effector in the imaging space;

based on the position data of the end effector, calculating a first directional vector between the fixed reference point and the end effector; and combining the first directional vector and a second directional vector between the end effector and the fixed end of the robot to calculate the resultant vector between the fixed reference point of the 3D imaging device and the fixed end of the robot.

14. The method as claimed in claim 11, wherein processing the 3D image of a body containing the target comprises:

extracting position data of the target in the imaging space; and based on the calibration of the robot, converting the position data of the target in the imaging space into the location data of the target in the integrated space.

15. The method as claimed in claim 11, wherein aligning the elongated tool with the target comprises a coarse adjustment of the elongated tool involving a displacement of the elongated tool along x, y or z axes and a fine adjustment of the elongated tool involving adjustment of an angular orientation of the elongated tool relative to a pivot point.

16. The method as claimed in claim 15, wherein adjusting the angular orientation of the elongated tool comprises:
actuating a plurality of arms linking a base and a platform of an adjustment mechanism, thereby moving the platform along a plane parallel to the base.

17. The method as claimed in claim 16, wherein the adjustment mechanism comprises parts made of materials with different radiolucencies, and wherein the step of processing the preliminary 3D image comprises obtaining position data of radiopaque parts of the adjustment mechanism for calibration of the robot.

18. The method as claimed in claim 16 or 17, wherein the method further comprises:
identifying a selected line in alignment with the target on the 3D image of the body; and generating an imaginary conical space that tapers along the line with an apex of the conical space disposed at the target and an axis of the conical space aligned with the line, wherein the conical space provides a boundary to the fine adjustment of the elongated tool.

19. The method as claimed in claim 18, wherein automatically controlling the manipulator comprises:
during the coarse adjustment of the robot, automatically controlling the manipulator to move the elongated tool into the conical space based on the formula $d \leq r-w$, wherein d=the closest distance between a centre of working radius of the adjustment mechanism and the axis of the conical space;

r (x)=a radius of the conical space corresponding with measurement of d;

w=the maximum working radius of the adjustment mechanism.

20. A method of striking an occluded target using an elongated tool, the method comprising the steps of:
aligning a longitudinal axis of the elongated tool with the target using the method as claimed in claim 11;

calculating a striking distance between the target and a tip of the elongated tool at alignment; and advancing the elongated tool toward the target based on the calculated striking distance.

* * * * *